United States Patent
O'Rourke (10) Patent No.: US 7,404,140 B2
(45) Date of Patent: Jul. 22, 2008

(54) SYSTEM FOR MANAGING FORM INFORMATION FOR USE BY PORTABLE DEVICES

(75) Inventor: Kevin O'Rourke, Downingtown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 474 days.

(21) Appl. No.: 10/465,254

(22) Filed: Jun. 19, 2003

(65) Prior Publication Data

US 2004/0153965 A1   Aug. 5, 2004

Related U.S. Application Data

(60) Provisional application No. 60/444,147, filed on Jan. 31, 2003.

(51) Int. Cl.
   G06F 17/40    (2006.01)
   G06F 17/21    (2006.01)

(52) U.S. Cl. .................. 715/222; 715/221; 715/223; 715/224; 715/229

(58) Field of Classification Search .............. 715/505, 715/506, 507, 511, 221, 222, 223, 224, 229
See application file for complete search history.

(56) References Cited

U.S. PATENT DOCUMENTS

| | | | | |
|---|---|---|---|---|
| 5,619,708 A | * | 4/1997 | Ho | 715/506 |
| 5,704,029 A | | 12/1997 | Wright, Jr. | 395/149 |
| 5,764,992 A | | 6/1998 | Kullick et al. | |
| 5,857,967 A | | 1/1999 | Frid et al. | 600/301 |
| 6,119,137 A | | 9/2000 | Smith et al. | 707/523 |
| 6,128,661 A | | 10/2000 | Flanagin et al. | 709/227 |
| 6,151,643 A | * | 11/2000 | Cheng et al. | 710/36 |
| 6,195,667 B1 | | 2/2001 | Duga et al. | 705/513 |

(Continued)

FOREIGN PATENT DOCUMENTS

WO    0169444 A2    9/2001

(Continued)

OTHER PUBLICATIONS

Courter et al., Mastering Microsoft Office 2000 Professional Edition, 1999, Sybex Inc., pp. 225-237.*

(Continued)

*Primary Examiner*—Joshua D Campbell
(74) *Attorney, Agent, or Firm*—Alexander J. Burke (57) ABSTRACT

A system updates a portable processing device with the latest version of customized data collection forms and associated data for use in acquisition of particular types of data for communication to a remote clinical information database. A system for providing forms for use in data collection by a portable processing device includes a form creator for creating an electronic form for use in collecting data, in response to user command. The system includes a repository of created electronic forms and a form version detector for detecting whether a newer version of a form currently stored in a portable processing device is available. A communication processor initiates communication of data representing a newer version form derived from the repository to the portable processing device in response to detection of availability of the newer version. The form creator generates data associated with an individual created form for use in providing a button displayed in an image on a portable processing device and includes a preview generator for initiating generation of a preview image of a form under construction based on user entered form configuration information.

15 Claims, 9 Drawing Sheets

U.S. PATENT DOCUMENTS

| | | | | |
|---|---|---|---|---|
| 6,345,278 | B1 * | 2/2002 | Hitchcock et al. | 707/100 |
| 6,606,604 | B1 * | 8/2003 | Dutta | 705/26 |
| 6,816,630 | B1 * | 11/2004 | Werth et al. | 382/287 |
| 2002/0194028 | A1 | 12/2002 | Johnston et al. | 705/3 |
| 2003/0023626 | A1 * | 1/2003 | Bretti | 707/506 |
| 2003/0037069 | A1 | 2/2003 | Davison | 707/200 |
| 2003/0101238 | A1 | 5/2003 | Davison | 709/219 |

OTHER PUBLICATIONS

MDeverywhere Core http://www.mdeverywhere.com pp. 2.
MDEveryCharge http://www.mdeverywhere.com pp. 10.
EveryNote http://www.mdeverywhere.com pp. 7.
EveryReference http://www.mdeverywhere.com 1 page.
EveryOrder http://www.mdeverywhere.com 1 page.
patientkeeper Charge Capture Application suite www.patientkeeper.com pp. 6.
patientkeeper "Clinical Application suite" pp. 13.
patientkeeper "Infrastructure" pp. 3.
patientkeeper "Patientkeeper Personal" 1 page.
"Four top hospitals standardise on PatientKeeper's Mobilizer Platform to make physicians mobile and wireless" *Virtual Medical Worlds* http://www.hoise.com/vmw/02/articles/vmw/LV-VM-03-02-23.html.
"Is the Future in the Palm of Your Hand"? *Health Data Management* Jan. 2002 www.HEALTHDATAMANAGEMENT.COM.
"The Future of medicine is in your hands," *Palm* Healthcare solutions http://www.palm.com/solutions/healthcare/ pp. 5.

\* cited by examiner

Administration

Field Definition                                    User: N/A

Administration
Customize
PDAccess
▲ Fields         Field Name: _______    Observation Code: _______         Field List
  Forms          Field Label: _______
                 Field Type:  ○ Data Entry  ○ ListBox  ○ CheckBox         Field Name        Obs Code
                                                                          Temperature       TEMP
                                                                          Temperature Source  TEMP-SRC To modify or delete a field, select the field from the list on the right.

To add a new field, enter the field information in the form above and press the Add Field button below.

FIG. 5

Value if checked: [          ]

FIG. 8

Use value list from field named: [          ]

or, Specify a list of values below:

```
Oral
Axillary
Rectal
Tympanic
Temporal
Core
```

FIG. 7

Required?  ○ Yes  ○ No

Maximum Number of Characters: [          ]

Minimum Value: [          ]

Maximum Value: [          ]

FIG. 6

Form Definition

Status: Test    Form Type: Results Charting
*Form Name:    Model Vitals Charting Form - Copy
*Form Label:   Chart Vitals ☑ Create Save Button        ☑ Create Send Button

| Line | Pos | Type | | | | |
|---|---|---|---|---|---|---|
| 1 | 1 | ○ Field ● Label ○ Spacer | Label Text: | Bed: | | |
| 1 | 2 | ● Field ○ Label ○ Spacer | Field Name: | Patient Room/Bed | | |
| 1 | 3 | ○ Field ● Label ○ Spacer | Label Text: | Age: | | |
| 1 | 4 | ● Field ○ Label ○ Spacer | Field Name: | Patient Age | | |
| 1 | 5 | ○ Field ● Label ○ Spacer | Label Text: | Sex: | | |
| 1 | 6 | ● Field ○ Label ○ Spacer | Field Name: | Patient Sex | | |
| 2 | 1 | ○ Field ● Label ○ Spacer | Label Text: | Adm: | | |
| 2 | 2 | ● Field ○ Label ○ Spacer | Field Name: | Patient Admit Date | | |
| 2 | 3 | ○ Field ● Label ○ Spacer | Label Text: | MR: | | |
| 2 | 4 | ● Field ○ Label ○ Spacer | Field Name: | Patient MedRec Number | | |
| 3 | 1 | ○ Field ● Label ○ Spacer | Label Text: | AtnDr: | | |
| 3 | 2 | ● Field ○ Label ○ Spacer | Field Name: | Patient Atn Dr Name | | |

Save | Cancel | Help

Form Preview
☑ Show Preview        ☐ Grid

Chart Vitals        Bloom, Valerie
Bed: 423-01 Age: 65 Sex: F
Adm: 31 May 03 MR: AA006562
AtnDr: Barclay, Joseph M.D.
User: USER00
Obs Date: 15 May 03    Change
Obs Time: 15:30    Change Temp: [   ] [-Select-▼]
Pulse: [   ] [-Select-▼]
Resp Rate: [   ]

Blood Pressure:
1: [   ] / [   ]
   [-Select-▼] [-Select-▼]
2: [   ] / [   ]
   [-Select-▼] [-Select-▼]
3: [   ] / [   ]
   [-Select-▼] [-Select-▼]
Wgt: lbs [   ] oz [   ] [-Select-▼]
Hgt: ft [   ] in [   ] [-Select-▼]
Fetal Heart Rate: [   ]

FIG. 9

| 450 ↘ | 453 ↘ |
|---|---|
| Form name | Link Text |
| ModelVitals Charting Form - Copy | Chart Vitals |
| Other forms names… | Other text links… |
| … | … |

Chart Vitals  Bloom, Valerie

Charting on 08 Feb 03 at ▼ 06:00

Temp:       [........]    ▼ --Select--
Pulse:       [........]    ▼ --Select--
Resp. Rate:  [........]
BP:          [........]/[........]
    ▼ --Select--   ▼ --Select--
Weight:    lbs[........]oz[........]
    ▼ --Select--
Height:    ft[........]in[........]
    ▼ --Select--

FIG. 12

SYSTEM FOR MANAGING FORM INFORMATION FOR USE BY PORTABLE DEVICES

This is a non-provisional application of provisional application serial No. 60/444,147 by K. O'Rourke filed 31 Jan., 2003.

FIELD OF THE INVENTION

This invention concerns a system and user interface supporting creation, and communication of electronic forms and associated data between a portable processing device and a remote system including a server or other device.

BACKGROUND OF THE INVENTION

Portable processing devices are increasingly being used to permit a physician to access and search current patient record information at the point of care. Ideally, a portable device, such as a palmtop computer, has a display large enough to easily view a patient record yet small enough to facilitate portability. However, available portable systems for processing patient record information are limited in their capabilities for securely acquiring, accessing, transferring and updating patient record information and in their capabilities for creating and navigating image menus supporting the location and access of desired patient record data by a user. Specifically, available portable systems are limited in their capabilities for collecting and processing patient data at the point of care and in transferring the collected data to a remote system such as a patient record management system. Typically hospital personnel use a data collection form to acquire patient data such as blood pressure, pulse, vital signs etc. However, the data collection requirements of hospitals and other healthcare providers (including, clinics, physicians, group practices, care facilities etc.) differ. It is desirable to provide a portable processing system accommodating different forms for use by different hospitals and for collection of different types of data. It is further desirable that such a system supports management and transfer of forms and associated collected data as well as ancillary information within a network hosting portable processing devices. A system according to invention principles addresses these requirements and associated problems.

SUMMARY OF INVENTION

A system updates a portable processing device with the latest version of customized data collection forms and associated data for use in acquisition of particular types of patient data (e.g., vital signs, physician and nursing notes, orders for tests, and medications to be administered) for communication to a remote clinical information database. A system for providing forms for use in data collection by a portable processing device includes a form creator for creating an electronic form for use in collecting data, in response to user command. The system includes a repository of created electronic forms and a form version detector for detecting whether a newer version of a form currently stored in a portable processing device is available. A communication processor initiates communication of data representing a newer version form derived from the repository to the portable processing device in response to detection of availability of the newer version.

In a feature of the invention a preview generator initiates generation of a preview image of a form derived from user entered configuration information.

In another feature of the invention, the form creator generates data associated with an individual created form for use in providing a button for initiating display of the form on a portable processing device.

DETAILED DESCRIPTION OF THE DRAWING

Figure 1:
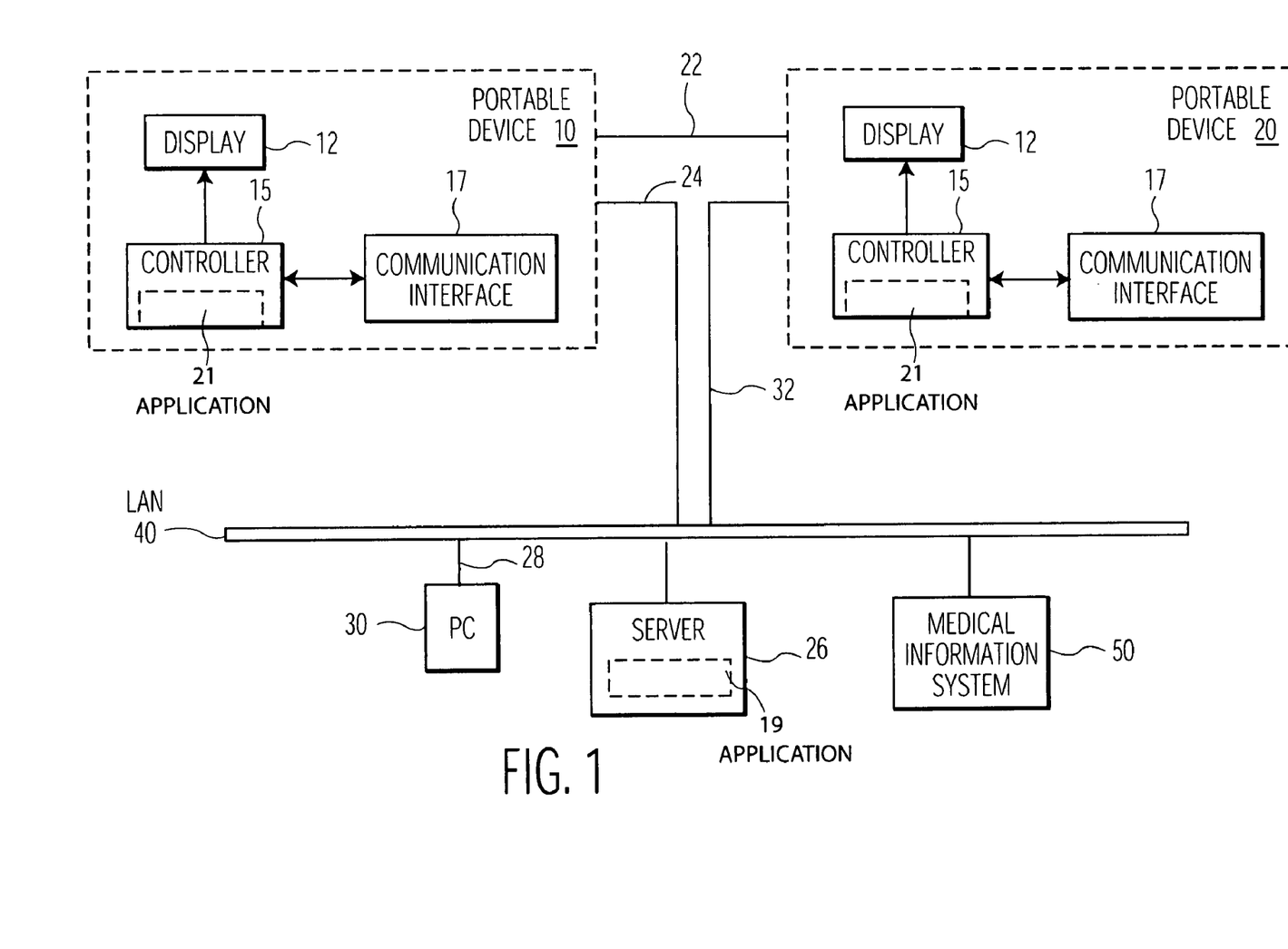
FIG. 1 shows a network system supporting data collection form creation and management as well as the transfer of collected patient data to a remote clinical information database, according to invention principles.

FIG. 1 shows a network system supporting data collection form creation and management as well as the transfer of collected patient data to a remote clinical information database. Patient information acquired following user data entry via a portable processing device is uploaded to a patient record repository and may be printed or passed to another portable processing device using an infrared serial connection or another connection. A user of a portable processing device is able to download a complete medical record or a portion of a record for either, a specific patient, or a user-specified list of patients from a patient record repository using a variety of communication links. Such communication links include, for example, serial connections to PC or server serial ports using serial cradles or infra-red transceiver connections, Ethernet connections to PC or server Ethernet ports using Ethernet cradles or infra-red transceiver connections and other WAN (Wide Area Network) and LAN (Local Area Network) and wireless connections.

The network architecture of FIG. 1 is exemplary only. The portable processing devices may operate in a variety of network environments involving one or more hierarchically arranged LANs or WANs including Ethernet-compatible LANs (used to connect different hospital departments, for example) and multiple Medical Interface Buses (MIBs) for corresponding multiple patients. In addition, a portable processing device is able to access the Internet via a firewall and other intra-nets (not shown) using a dial-up telephone connection, ADSL, cable modem or other types of connection. Individual portable processing devices are Internet Protocol (IP) compatible but may also employ other protocols supporting communication connectivity among the networked devices. The system includes a software application (application 19 of FIG. 1) executing on web server 26 that enables a user to create, manage and store data collection forms suitable for use on a portable processing device, such as a palm or lap top computer, PocketPC or PDA (Personal Data Assistant). Created forms are advantageously downloaded automatically to a clinician's PDA, for example, the next time the portable device accesses patient information for download. This system advantageously distributes the latest version of forms to portable devices without requiring synchronization of the devices with a form distribution application.

The network system of FIG. 1 supports the acquisition and communication of patient medical record information using a data collection form created by a user employing application 19 accessed using Personal computer (PC) 30 via Ethernet connection 28 and LAN 40. Form creation and management application 19 is browser and Internet compatible and resides on server 26. Application 19 supports creation of patient data collection forms as standard HTML (Hyper Text Markup Language) files stored in a server 26 file directory system for subsequent access and modification as required. Created forms are tested either on PC 30 using a portable processing device software emulator or are tested on a real portable processing device. Forms ready for distribution are placed in a separate server 26 file directory for subsequent communication to portable processing devices 10 and 20. Patient medical record information collected using a data collection form is securely transferable between portable devices 10 and 20 via an infra-red serial port connection 22 or via Ethernet connections 24 and 32 and LAN 40. The collected patient medical record information is also communicated to medical record information repository system 50. A clinician enters a command on portable device 10 (or 20) to access server 26 to download patient data from medical information system 50 or to upload patient data to system 50. Application 19 on server 26 compares the version (e.g., time and date of creation) of the forms on portable device 10 with the version of corresponding forms stored within server 26 and in response to a version difference, application 19 initiates communication of the latest version of the forms to portable device 10.

Portable devices 10 and 20 each comprise a controller 15 for processing data and commands received via communication interface 17 as well as via data entry from attached data entry devices including a keyboard and mouse or other cursor controls (not shown to preserve drawing clarity). Application 21 executes on controller 15 and manages display of data collection forms, menus and acquired information on display 12. Application 21 also manages bidirectional communication with, server 26, medical information system 50 and other portable processing devices and Internet and other Intra-net connections via communication interface 17. Portable processing devices 10 and 20, using controllers 15 and interfaces 17, directly bi-directionally communicate with each other via infra-red serial port connection 22 and also communicate with each other and information system 50 and the Internet and other intra-net systems, for example, using other communication links. Such other communication links include a serial connection to PC 30 and from PC 30 via Ethernet connection 28 to LAN 40 and system 50 (or the Internet and other external connections via a firewall, for example). Alternatively device 10 may directly communicate via Ethernet connection 24 with LAN 40 and system 50. Similarly, portable device 20 may directly communicate via Ethernet connection 32 with LAN 40 and system 50. Further, the serial and Ethernet connections may also involve wireless connections including infrared or other connections. Thereby portable devices 10 and 20 communicate data collection forms and associated data to server 26 and medical information system 50

Figure 2:
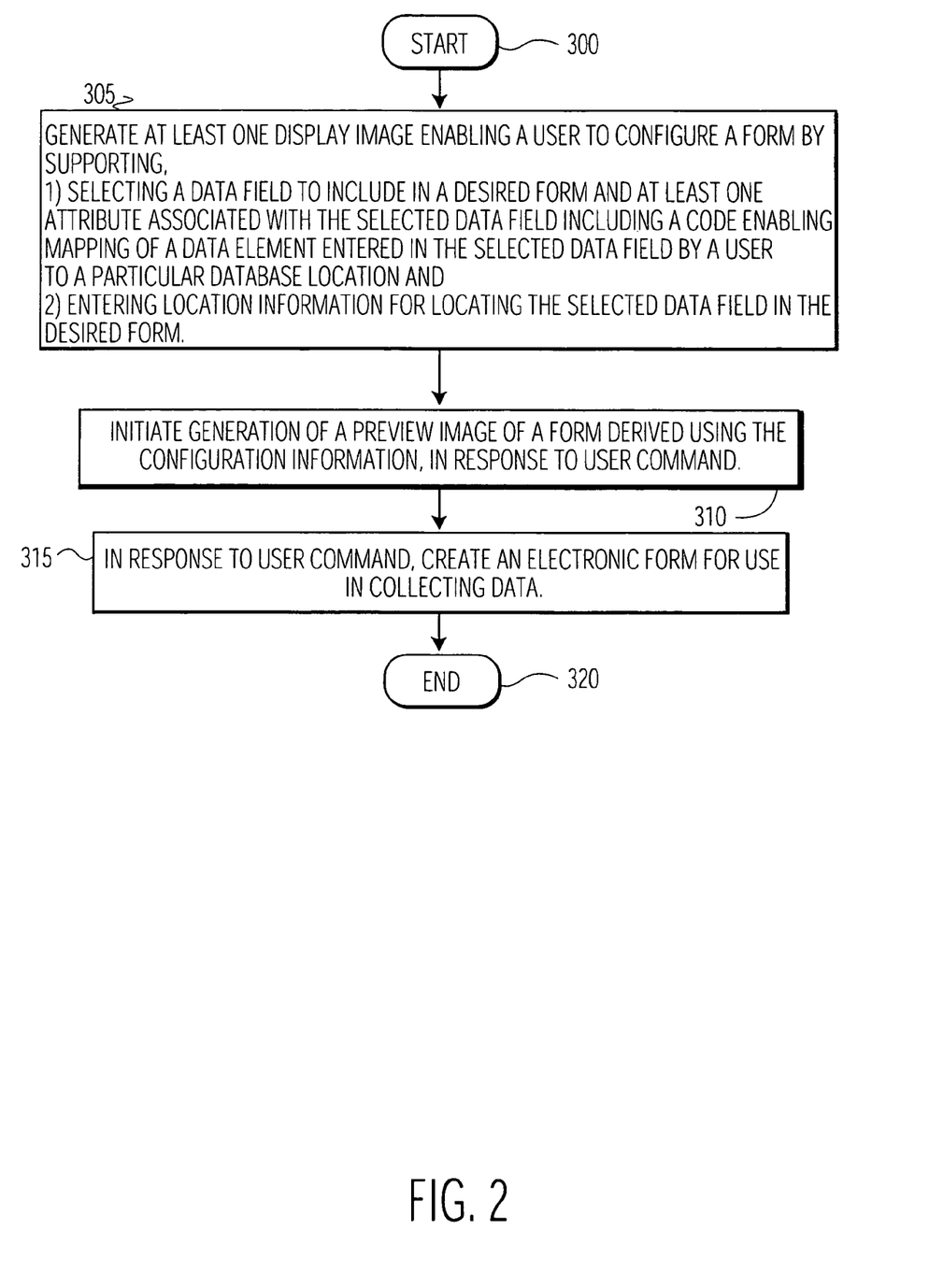
FIG. 2 shows a flowchart of a process for creating a data collection form for use by a portable processing device in collecting patient data, according to invention principles.
Figure 5:
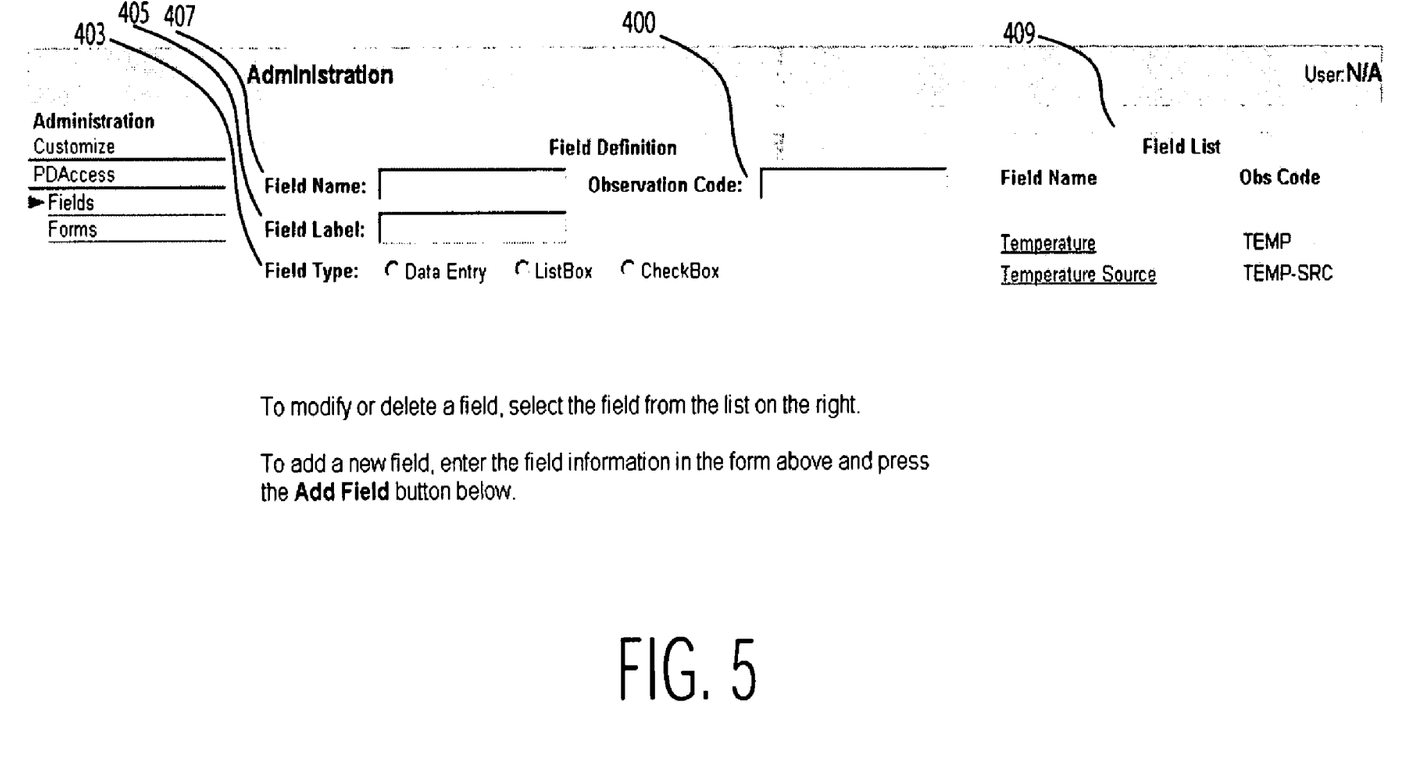
FIG. 5 shows a user interface image menu supporting creation of data fields in a portable processing device data collection form, according to invention principles.

FIG. 2 shows a flowchart of a process performed by application 19 executing on server 26, in response to user command entered via PC 30, for creating a data collection form for use by portable processing device 10 in collecting patient data. A user creates a data collection form by employing form creation and management application 19 performing the steps of the Flowchart of FIG. 2 and executing on server 26 accessed using Personal computer (PC) 30 via Ethernet connection 28 and LAN 40. In step 305 of FIG. 2, following the start at step 300, application 19 in response to user command, initiates generation of one or more display images enabling a user to enter configuration information for creating a desired form. For this purpose, a generated display image supports user selection of a data field for inclusion in a desired data collection form. FIG. 5 shows a user interface image menu supporting creation of data fields in a portable processing device data collection form. The user interface image of FIG. 5 is initiated in response to user selection of a form builder button in a menu displayed on PC 30. A user employs the FIG. 5 image to establish a data field in creating a form for collecting individual patient parameters such as temperature and blood pressure, for example.

The generated display image of FIG. 5 also supports user selection of at least one attribute associated with a selected data field. Such an attribute includes a code (observation code 400) enabling mapping of data entered in a particular data field in a form to a particular location in a database. The code is used to identify a corresponding data field and an associated storage location in a host database. Application 19 associates a code with both, a particular data field (e.g., patient temperature data field) in a data collection form being created and with a corresponding location in the host database (in server 26 or information system 50). Consequently, individual fields in the host database have a unique identifier, for example, Patient Temperature may be identified by the text string PAT-TEMP. Thereby, in response to user entry of a patient temperature value via a created data collection form, device 10 communicates the entered value and associated code (e.g. by sending the string "PAT-TEMP=98.6") to application 19 on server 26. Application 19 uses the code to store the received value in the correct location in the host database in server 26 or system 50. Window 409 of the interface image of FIG. 5 lists user created data fields sorted by name and also shows the observation (identification) code associated with each data field.

Figure 6:
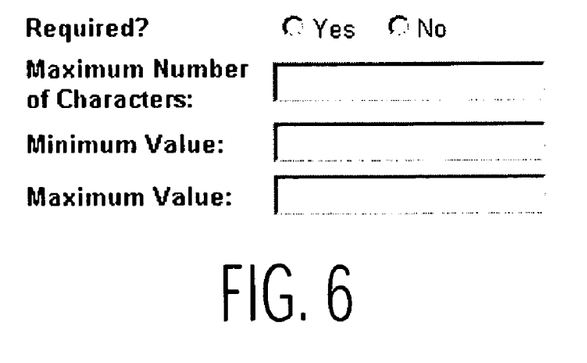
FIGS. 6-8 show data entry elements used with data fields incorporated in a portable processing device data collection form, according to invention principles.
Figure 7:
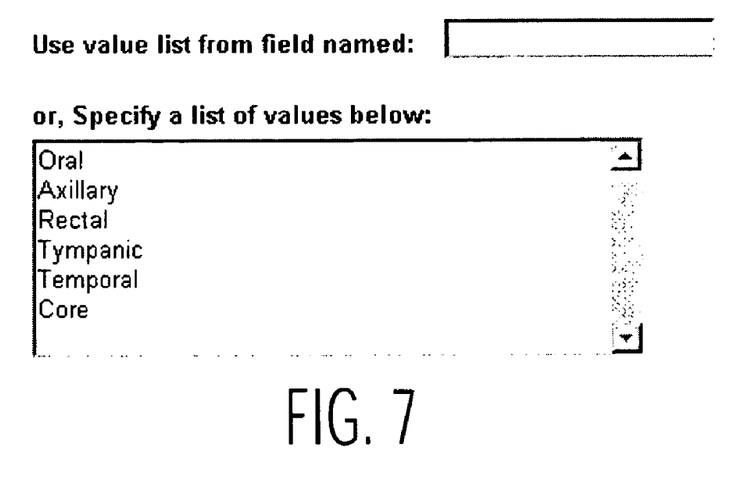
Figure 8:
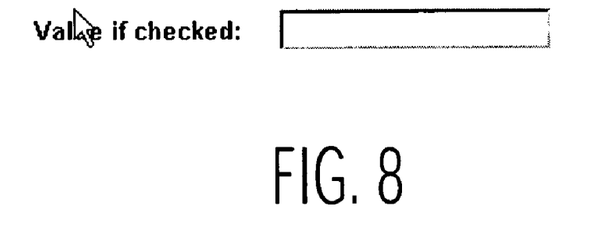

Other attributes selectable by a user for association with a selected data field include, a data field name 407 (e.g., Temperature, Blood Pressure), a data field label 405 to display together with a data field in a created form and a type of data entry box 403 for use in a data field in a created form. The type of data entry box 403 may comprise a text box, list box, checkbox or radio button, for example. FIGS. 6-8 illustrate exemplary data entry boxes selectable by a user via a generated display image (in step 305 of FIG. 2). A user associates a selected data entry box with a data field in a data collection form via the FIG. 5 form configuration user interface image.

FIG. 6 illustrates a user selectable text data entry type of data field. This data entry field supports user selection of a specified: maximum number of characters that may be entered, a minimum value, a maximum value, and whether user data entry is required. Similarly FIG. 7 illustrates a list data entry type of data field enabling user selection of allowable data entry items. Further, FIG. 8 illustrates a checkbox or radio button data entry type of data field enabling a user to assign a value to be used if the button is checked.

Figure 9:
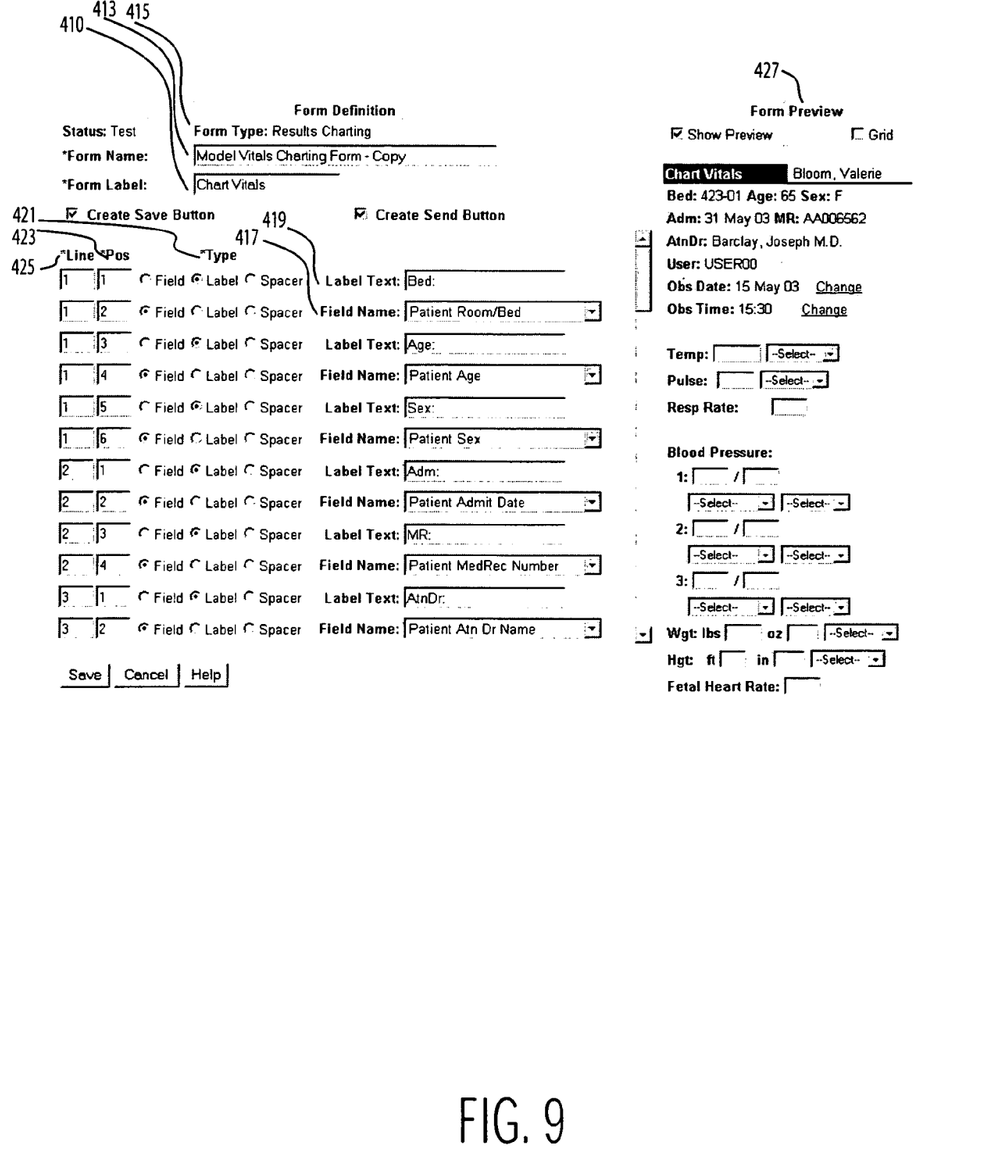
FIG. 9 shows a user interface image menu supporting creation of a portable processing device data collection form, according to invention principles.

In response to user command, application 19 in step 310 initiates generation of a composite user interface image shown in FIG. 9 supporting form creation and including a preview image of a form derived using configuration information entered in step 305. Application 19 updates the preview image in response to user entry of configuration information to give a continuously updated preview of a form as it is being created. Thereby, as fields are added to the form, preview window 427 shows the look of the form as it is being created. As a new field is added to the form it appears in the preview window. If there is an error when attempting to add a field, it does not appear in preview window 427 (in another embodiment the system automatically corrects an error and shows a corrected form layout). The FIG. 9 interface image enables a user to identify a form to be created by entering the form name 413 and form label 410. The resultant interface image shows the form type 415 and supports user entry of location information for positioning user selected elements including data fields, and associated labels and spaces (identified by type selector 421) in the form being created. The location information includes, a line number 425 identifying an image display line at which to locate a selected element and a position number 423 identifying a position along the selected line to locate the selected element. The associated data field name and label are selected by a user via items 417 and 419.

Figure 12:
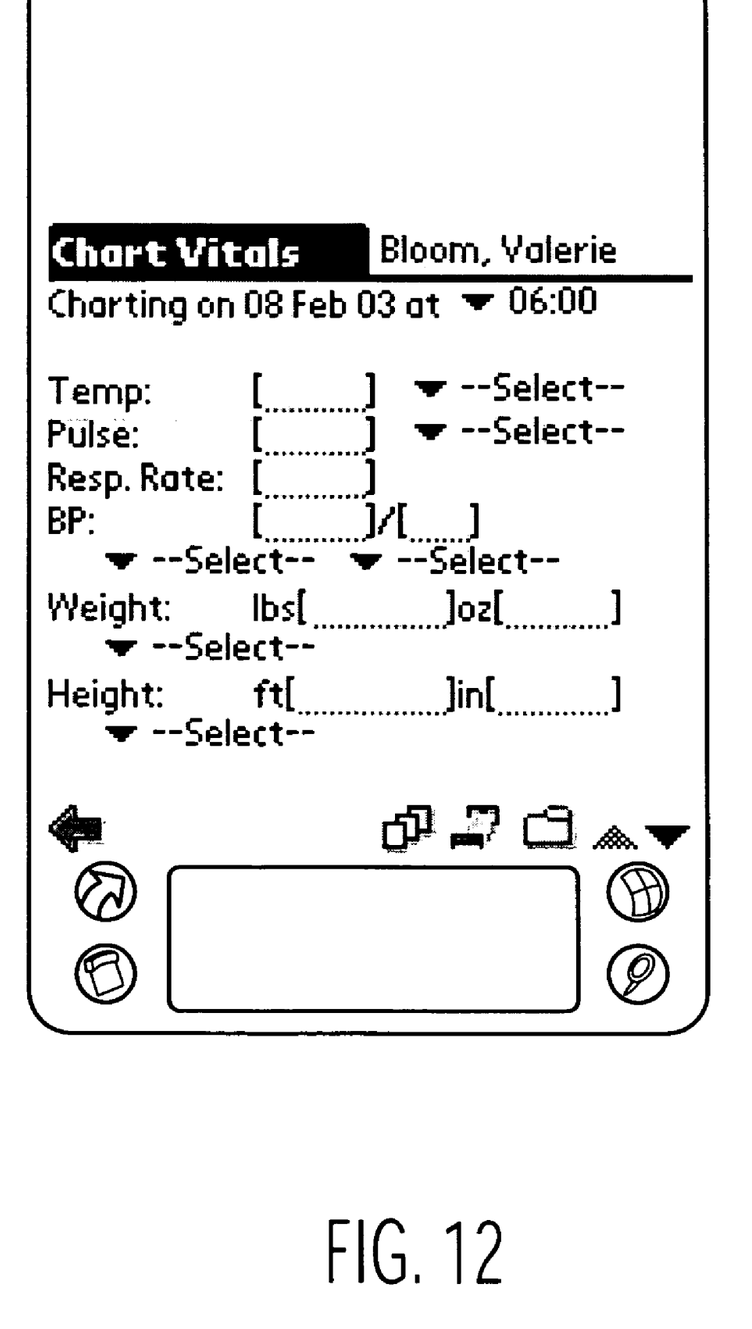
FIG. 12 shows a user interface image menu presenting a particular data collection form associated with a patient vital sign data, according to invention principles.

Application 19 in step 315 uses the configuration information entered in steps 305 and 310 to create an electronic data collection form as exemplified in the patient chart vital signs data collection form of FIG. 12, for use on portable device 10. In response to creation and storage of the data collection form in step 315 application 19 creates data associated with the form illustrated in the table of FIG. 10 for storage on server 26. The data associated with the form links the form name (e.g., Model Vitals Charting Form—Copy, item 450 FIG. 10, item 413 FIG. 9) with link text (e.g., Chart Vitals, item 453 FIG. 10, item 410 FIG. 9). The link text (Chart Vitals—form label 410 of FIG. 9) provides a user selectable link (or a button) displayed in an image on portable device 10. The process of FIG. 2 terminates at step 320.

Figure 3:
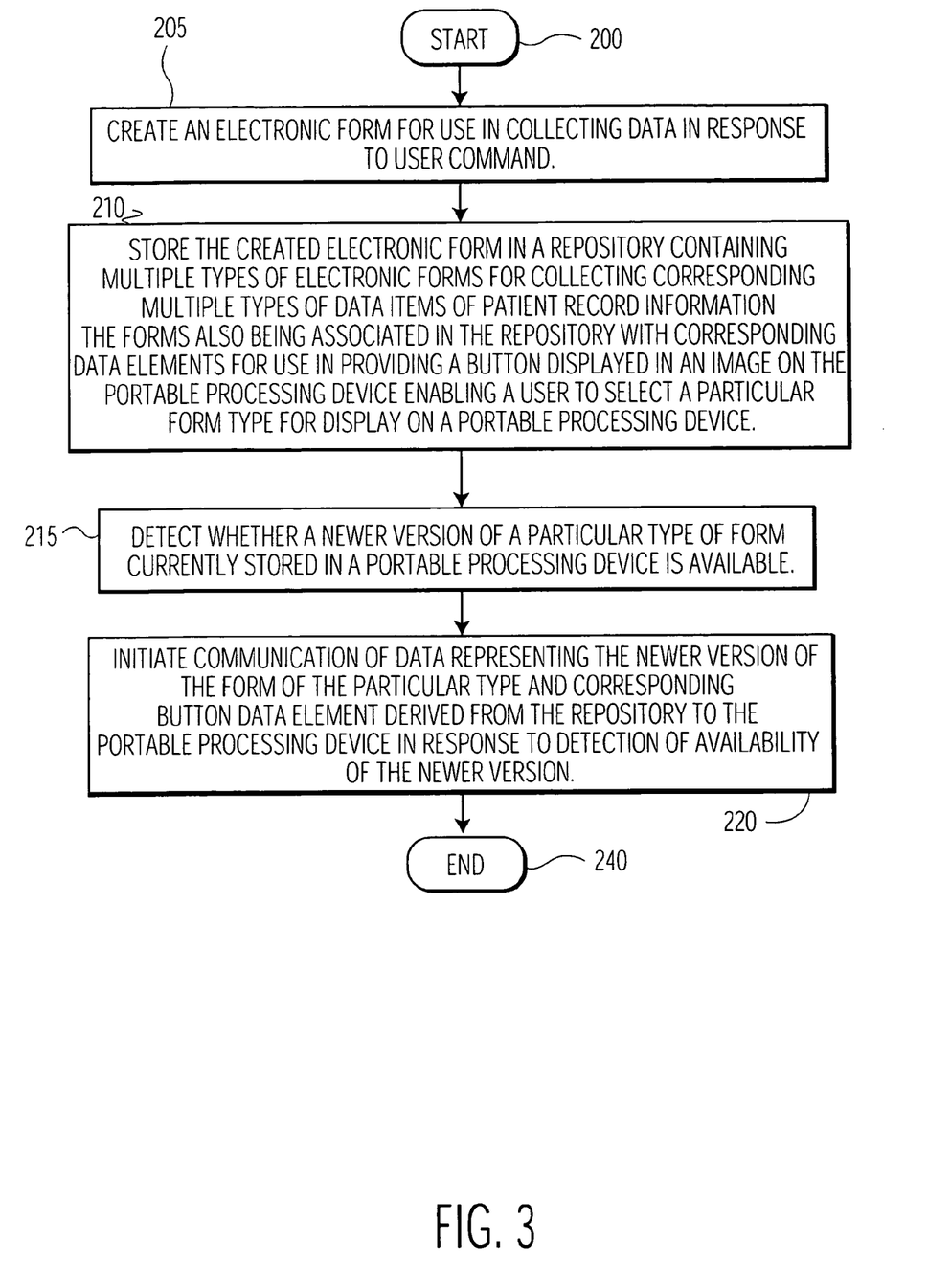
FIG. 3 shows a flowchart of a process for managing the transfer of a created data collection form to a portable processing device, according to invention principles.

FIG. 3 shows a flowchart of a process performed by application 19 for managing the transfer of a created data collection form to a portable processing device. In step 205 of FIG. 3, following the start at step 200, application 19 creates an electronic form in response to user command, using the process described in connection with FIG. 2. In step 210 of FIG. 3, application 19 in response to user command stores the created form in a repository on server 26 (or system 50) containing multiple different types of forms for collecting corresponding multiple different types of data items of patient record information. The different types of forms are used for collecting different types of data items associated with different sections of patient record information identified in a content index image displayed on portable device 10. Different organizations and different departments within an individual organization also employ different types of forms customized to particular organization or department requirements, for example. The different types of data items include, for example, order information, vital sign information, progress notes, physician notes, laboratory test results, imaging information, allergy information, medication information, nurses notes, immunization, encounter information or problem descriptions. The repository also associates individual forms with corresponding data elements for use in providing a button displayed in an image on portable processing device 10. Such a button enables a user to select a particular form type for display on device 10.

Application 19 in step 215 receives data collection form time and date stamp information (or other form version identification information) identifying time and date of creation of a form in at least one communication message from portable device 10. The time and date stamp information is communicated by device 10 to application 19 together with patient data collected via the form of a particular type. This is done in response to a user command to update electronic patient record information of a particular patient, for example. Application 19 automatically detects whether a newer version of the form of the particular type currently stored in a portable processing device is available. This is done by comparing form time and date stamp information (or other version identification data) received from portable processing device 10 with time and date stamps (or other version identification data) of forms stored in a repository in server 26 (or system 50). Other form version identification information may comprise a character string identifying a form version, for example. Alternatively, application 19 maintains a record of versions of forms communicated to portable processing device 10 and compares form version identification data of forms stored in the repository with version identification data in the record.

Figure 10:
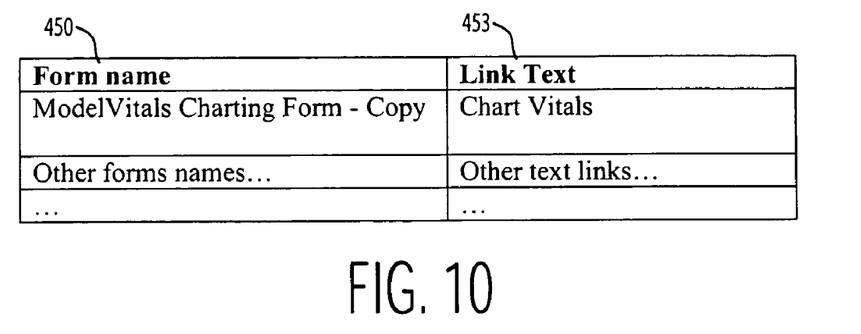
FIG. 10 shows a table associating data collection form identification names with corresponding user selectable links displayed in a portable processing device user interface image, according to invention principles.

Application 19 in step 220 retrieves data representing the newer version of the data collection form of the particular type derived from the repository in server 26 in response to a determination that a newer form version is available. Application 19 automatically initiates communication of the retrieved form representative data to portable device 10. Alternatively, application 19 sends data representing the latest form version to portable device 10 in response to a form update command. The form representative data is communicated to portable device 10 together with data associated with the particular form for use in providing a displayed link (or button). The data associated with the particular form for use in providing a displayed link is illustrated in the table of FIG. 10 and is retrieved from storage in server 26. This link data is generated during the form creation process as described previously in connection with FIG. 2 (step 315). The data associated with the form, links the form name (Model Vitals Charting Form—Copy, item 450 FIG. 10) with link text (Chart Vitals, item 453 FIG. 10).

In the preferred embodiment, the data collection forms are stored in a designated directory on the same web server (server 26) that clinicians use to download or upload patient information from system 50. In other embodiments the stored forms and patient record information are located on different servers or storage devices. The process of FIG. 3 terminates at step 240.

Figure 4:
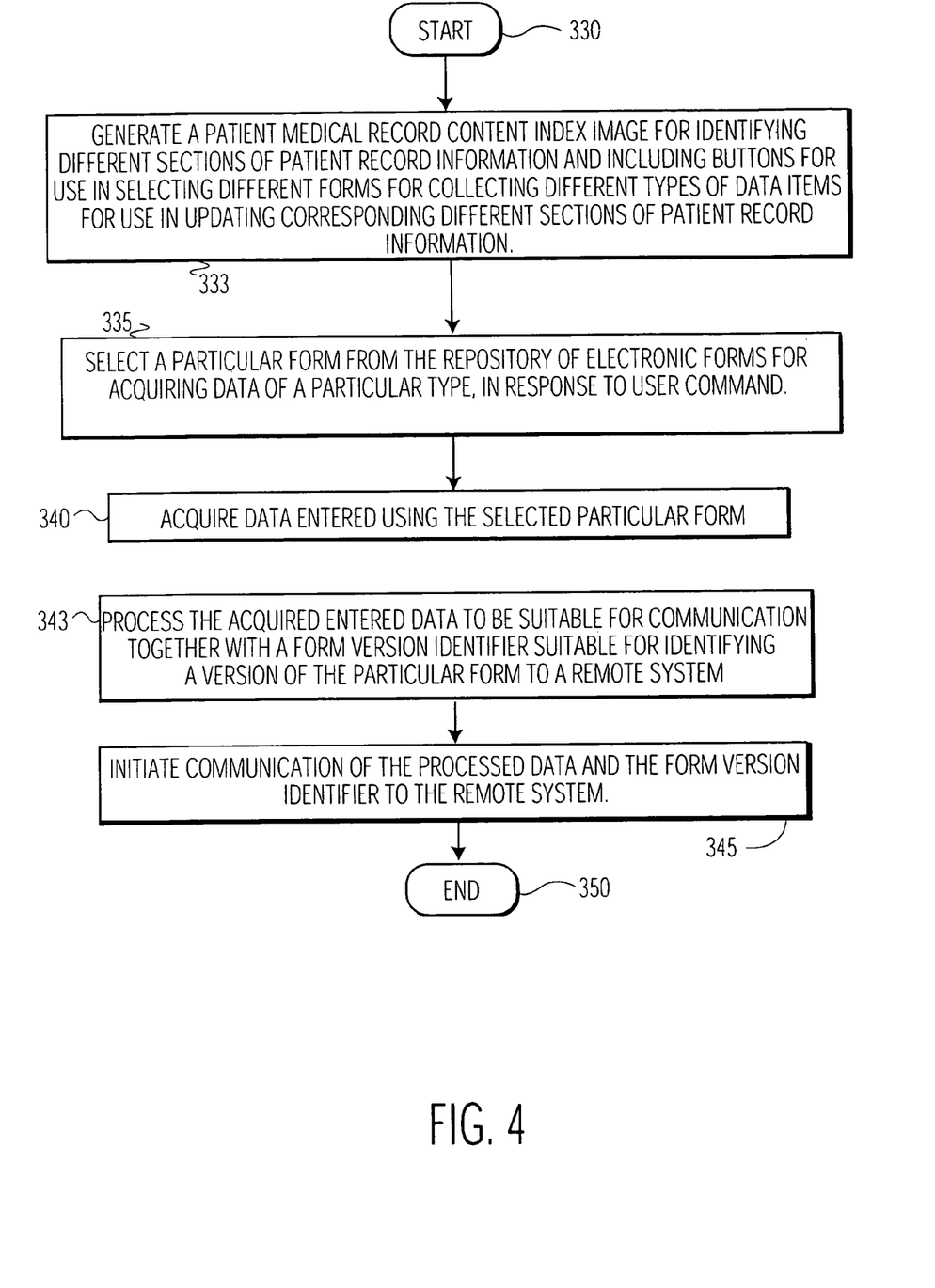
FIG. 4 shows a flowchart of a process for use by a portable processing device in applying a data collection form in acquiring and communicating patient data, according to invention principles.

FIG. 4 shows a flowchart of a process for use by portable processing device 10 in selecting and applying a data collection form in acquiring and communicating patient data, In step 333 of FIG. 4, following the start at step 330, application 21 of device 10 generates a patient medical record content index image (exemplified in FIG. 11) for identifying different sections of patient record information and including buttons for use in selecting different forms for collecting different types of data items. The different forms are stored in a repository in device 10 and are used to collect different types of data items for use in updating different sections of patient record information. The medical record content index image of FIG. 11 comprises a hyperlinked content index to each of the major sections of a patient chart such as Chemistry, Hematology, Vital Signs etc. as exemplified in elements 911-929 of FIG. 11.

A patient record content index is created dynamically by application 19 on server 26 as patient record information for a particular patient is generated and communicated by application 19 to processing device 10. Further, as application 19 collates individual sections of a patient record for communication to processing device 10, it also creates individual URL links to corresponding record sections for use in a patient record content index. Specifically, as a new section of patient record data is retrieved from a record repository, a name of that section (e.g. Chemistry) is identified and stored in a memory buffer as an HTML hyperlink tag pointing to the report section it references.

Figure 11:
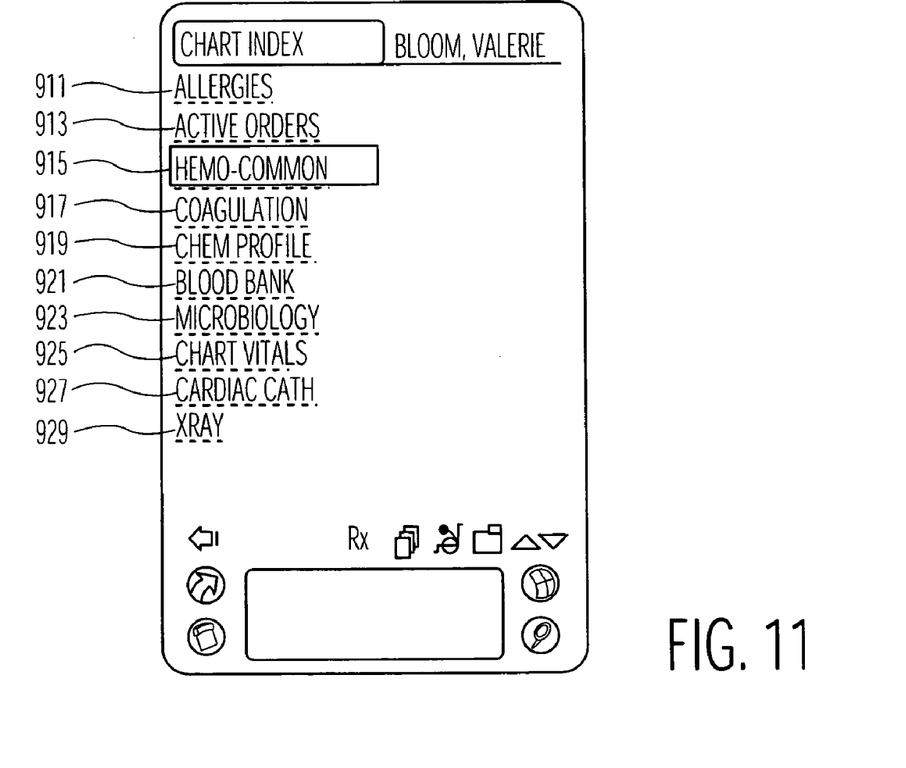
FIG. 11 shows a user interface image menu including user selectable links enabling user selection of a particular data collection form associated with a corresponding particular type of patient medical record data, according to invention principles.

In response to user selection of Chart Vitals link 925 in the medical record content index image of FIG. 11 displayed on device 10, application 21 in step 335 selects the Chart Vitals data collection form (exemplified in FIG. 12) from the device 10 repository, for acquiring patient vital sign data. For this purpose, application 21 of device 10 uses stored data associated with the particular form (illustrated in the table of FIG. 10) that links the form name (Model Vitals Charting Form—Copy, item 450 FIG. 10) with link text (Chart Vitals, item 453 FIG. 10). Application 21 uses this stored data to identify and retrieve a file comprising the Chart Vitals data collection form (illustrated in FIG. 12) stored on device 10 with the form name (Model Vitals Charting Form—Copy) in response to user selection of link 925 of the Chart Vitals image of FIG. 11. The Chart Vitals data collection form of FIG. 12 is accessed from device 10 memory and displayed on device 10. Application 21 acquires patient data entered using the Chart Vitals form in step 340 and in step 343 processes the acquired entered patient data to be suitable for communication to server 26. Application 21 incorporates a form version identifier (e.g., a time and date stamp identifier) identifying a version of the Chart Vitals form in the processed acquired entered patient data. In step 345, application 21 initiates communication of the processed data and the form version identifier to server 26. The processed data, including updated patient record information, is sent to update the patient record repository of system 50 or may be Emailed to another remote location or may be printed. The process of FIG. 4 terminates at step 350.

The architectures, user interface menus and processes presented in FIGS. 1-12 are not exclusive. Other architectures, processes and user interface menus may also be derived in accordance with the principles of the invention to accomplish the same objectives. Further, the inventive principles may be advantageously employed in any clinical health care information management system for facilitating distribution of patient and other information to multiple different locations.

What is claimed is:

1. A system in communication with at least one remote portable processing device for providing forms for use in data collection by a portable processing device, comprising:
    a display generator for generating at least one display image enabling a user to enter configuration information for creating a desired form, said configuration information supporting,
        selecting for inclusion in a desired form,
            a data field and
            at least one attribute associated with said selected data field comprising a code separate from said selected data field enabling mapping of a data element entered in said selected data field by a user to a particular location in a database, and
        entering location information for locating said selected data field in said desired form;
    a form creator for creating an electronic form for use in collecting data, in response to user command;
    a repository of created electronic forms;
    a form version detector for detecting whether a newer version of a form currently stored in a portable processing device is available; and
    a communication processor for initiating communication of data representing a newer version form derived from said repository to said portable processing device in response to detection of availability of said newer version using information received from said portable processing device.

2. A system according to claim 1, wherein
said communication processor automatically initiates communication of data representing said newer version form to said portable processing device and
said form version detector detects whether a newer version of a form currently stored in a portable processing device is available by at least one of, (a) comparing form version identification data in said information received from said portable processing device with version identification data of forms stored in said repository and (b) maintaining a record of versions of forms communicated to said portable processing device and comparing version identification data of forms stored in said repository with version identification data in said record.

3. A system according to claim 2, wherein
said form version identification data comprises at least one of, (a) a character string identifying a form version and (b) a time stamp identifying time of creation of a form and (c) a date stamp identifying date of creation of a form.

4. A system according to claim 1, wherein
said repository of created electronic forms includes a plurality of different types of forms for collecting a corresponding plurality of different types of data,
said form version detector determines whether a newer version of a particular type of form currently stored in said portable processing device is available, and
said communication processor initiates communication of data representing said newer version of a form of a particular type derived from said repository to said portable processing device in response to detection of availability of said newer version.

5. A system according to claim 1, wherein
said form version detector determines whether a newer version of a form is available in response to a received communication message from said portable processing device.

6. A system according to claim 1, wherein
said form creator creates data associated with an individual created form for use in providing a button displayed in an image on said portable processing device enabling a user to select said individual created form for display on said portable processing device in response to user selection of said button and
said communication processor initiates communication of said data associated with said individual created form with data representing a newer version of said individual form to said portable processing device in response to detection of availability of said newer version.

7. A system according to claim 1, further comprising:
a preview generator for initiating generation of a preview image of a form derived using said configuration information, in response to user command.

8. A system according to claim 1, wherein
said at least one attribute associated with said selected data field also includes at least one of, (a) a data field name, (b) a data field label to display on said desired form together with said data field and (c) a type of data entry box to use on said desired form for said data field.

9. A system according to claim 1, wherein
said location information includes at least one of, (a) a line number identifying a line to locate said selected data field and (b) a position number identifying a position along said line to locate said selected data field.

10. A system according to claim 1, wherein
said preview generator initiates generation of said preview image in a window in a composite image including said at least one display image and updates said preview image in response to user entry of configuration information to give a continuously updated preview of a form as it is being created.

11. A system for use in data collection and communication by a portable processing device, comprising:
a repository of a plurality of electronic forms for acquiring data of different type, said electronic forms created by user-entered configuration information supporting
selection of a data field to include in a desired form and
at least one attribute associated with said selected data field including a code enabling mapping of a data element in said selected data field by a user to a particular location in a database; and
location information for locating said selected data field in said desired form;
a selection processor for selecting a particular form from said repository in response to user command, said selected form being for acquiring data of a particular type;
an interface processor for acquiring data entered using said selected particular form and for processing said data to be suitable for communication together with a form version identifier identifying a version of said particular form to a remote system, said form version identifier being usable by said remote system to, automatically determine a newer version of said particular form is available and to automatically initiate download of said newer version of said particular form to said portable processing device; and a communication processor for initiating communication of said processed data and said form version identifier to said remote system.

12. A system according to claim 11, wherein
said form version identifier comprises at least one of, (a) a character string identifying a form version and (b) a time stamp identifying time of creation of a form and (c) a date stamp identifying date of creation of a form.

13. A system according to claim 11, including
a display generator for generating at least one image including a button for display on said portable processing device enabling selecting a particular form from said repository in response to user selection of said button.

14. A system according to claim 11, wherein
said plurality of electronic forms are associated with a plurality of different organizations.

15. A system in communication with at least one remote portable processing device for providing forms for use in data collection by a portable processing device, comprising:
a display generator for generating at least one display image enabling a user to enter configuration information for creating a desired form, said configuration information supporting,
selecting for inclusion in a desired form,
a data field and
at least one attribute associated with said selected data field comprising a code separate from said selected data field enabling mapping of a data element entered in said selected data field by a user to a particular location in a database, and
entering location information for locating said selected data field in said desired form; and
a preview generator for initiating generation of a preview image of a form derived using said configuration information, in response to user command;
a repository of created electronic forms;
a form version detector for detecting whether a newer version of a form currently stored in a portable processing device is available; and
a communication processor for automatically initiating communication of data representing a newer version form derived from said repository to said portable processing device in response to detection of availability of said newer version using information received from said portable processing device by comparing form version identification data in said information received from said portable processing device with version identification data of forms stored in said repository.

* * * * *